United States Patent
Tojo et al.

(10) Patent No.: US 9,829,082 B2
(45) Date of Patent: Nov. 28, 2017

(54) BENDING OPERATION SYSTEM

(71) Applicant: OLYMPUS CORPORATION, Tokyo (JP)

(72) Inventors: Ryo Tojo, Hachioji (JP); Jun Hane, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 741 days.

(21) Appl. No.: 14/252,029

(22) Filed: Apr. 14, 2014

(65) Prior Publication Data

US 2014/0222214 A1 Aug. 7, 2014

Related U.S. Application Data

(63) Continuation-in-part of application No. PCT/JP2012/076495, filed on Oct. 12, 2012.

(30) Foreign Application Priority Data

Oct. 14, 2011 (JP) .................................. 2011-227113

(51) Int. Cl.
*A61B 1/00* (2006.01)
*F16H 21/54* (2006.01)
(Continued)

(52) U.S. Cl.
CPC ......... *F16H 21/54* (2013.01); *A61B 1/00006* (2013.01); *A61B 1/0052* (2013.01);
(Continued)

(58) Field of Classification Search
CPC . A61B 1/0051; A61B 1/0057; A61B 1/00006; A61B 1/0052; F16H 21/54; G02B 23/2476; A61M 25/0147
(Continued)

(56) References Cited

U.S. PATENT DOCUMENTS

2001/0027268 A1* 10/2001 Kato .................... A61B 1/0051
600/152
2002/0165432 A1* 11/2002 Matsui ................. A61B 1/0016
600/145

(Continued)

FOREIGN PATENT DOCUMENTS

JP 61-87530 A 5/1986
JP 3-16901 U 2/1991
(Continued)

OTHER PUBLICATIONS

International Preliminary Report on Patentability together with the Written Opinion of the International Searching Authority dated Apr. 24, 2014 from related International Application No. PCT/JP2012/076495.

(Continued)

*Primary Examiner* — Anhtuan T Nguyen
*Assistant Examiner* — Jae Woo
(74) *Attorney, Agent, or Firm* — Scully, Scott, Murphy & Presser, P.C.

(57) ABSTRACT

A bending operation system includes an elongated tubular portion including a bending portion, a first linear member and a second linear member which cause the bending portion to bend, and a drive portion which displaces the first linear member and the second linear member. The bending operation system further includes a first displacement detector which acquires a displacement of the first linear member as a first displacement, a second displacement detector which acquires a displacement of the second linear member as a second displacement, and a calculator which calculates operation assist information by use of one or both of the first displacement and the second displacement.

14 Claims, 12 Drawing Sheets

(51) Int. Cl.
*G02B 23/24* (2006.01)
*A61B 1/005* (2006.01)
*A61M 25/01* (2006.01)

(52) U.S. Cl.
CPC ........ *A61B 1/0057* (2013.01); *G02B 23/2476* (2013.01); *A61M 25/0147* (2013.01)

(58) Field of Classification Search
USPC .................................. 600/146, 149; 604/528
See application file for complete search history.

(56) References Cited

U.S. PATENT DOCUMENTS

| | | | |
|---|---|---|---|
| 2004/0049097 A1* | 3/2004 | Miyake | A61B 1/00039 600/150 |
| 2004/0138530 A1* | 7/2004 | Kawai | A61B 1/0016 600/152 |
| 2007/0106114 A1* | 5/2007 | Sugimoto | A61B 1/31 600/117 |
| 2007/0173694 A1* | 7/2007 | Tsuji | A61B 1/0005 600/146 |
| 2008/0221592 A1* | 9/2008 | Kawai | A61B 1/0055 606/130 |
| 2010/0204547 A1* | 8/2010 | Tanaka | A61B 1/0051 600/145 |
| 2011/0257480 A1* | 10/2011 | Takahashi | A61B 1/00147 600/106 |
| 2011/0275896 A1* | 11/2011 | Tanaka | A61B 1/00006 600/118 |
| 2011/0282154 A1* | 11/2011 | Umemoto | A61B 1/0051 600/152 |
| 2011/0295063 A1* | 12/2011 | Umemoto | A61B 1/008 600/109 |
| 2012/0265007 A1* | 10/2012 | Moriyama | A61B 1/0055 600/104 |
| 2013/0096423 A1* | 4/2013 | Yamamoto | A61B 1/00006 600/424 |
| 2013/0102960 A1* | 4/2013 | Miyoshi | A61B 1/00066 604/95.04 |
| 2013/0144275 A1* | 6/2013 | Umemoto | A61B 1/00006 606/1 |

FOREIGN PATENT DOCUMENTS

| | | |
|---|---|---|
| JP | H09-010172 A | 1/1997 |
| JP | 2002-264048 A | 9/2002 |
| JP | 3397940 B2 | 4/2003 |

OTHER PUBLICATIONS

Japanese Office Action dated Jul. 21, 2015 from related Japanese Patent Application No. 2011-227113, together with an English language translation.
Extended Supplementary European Search Report dated May 8, 2015 from related European Application No. 12 83 9517.5.
English abstract only of corresponding JP H09-010172 A.
International Search Report dated Dec. 25, 2012 issued in PCT/JP2012/076495.
Chinese Office Action dated Aug. 4, 2015 from related Chinese Patent Application No. 201280049992.6, together with an English language translation.

* cited by examiner

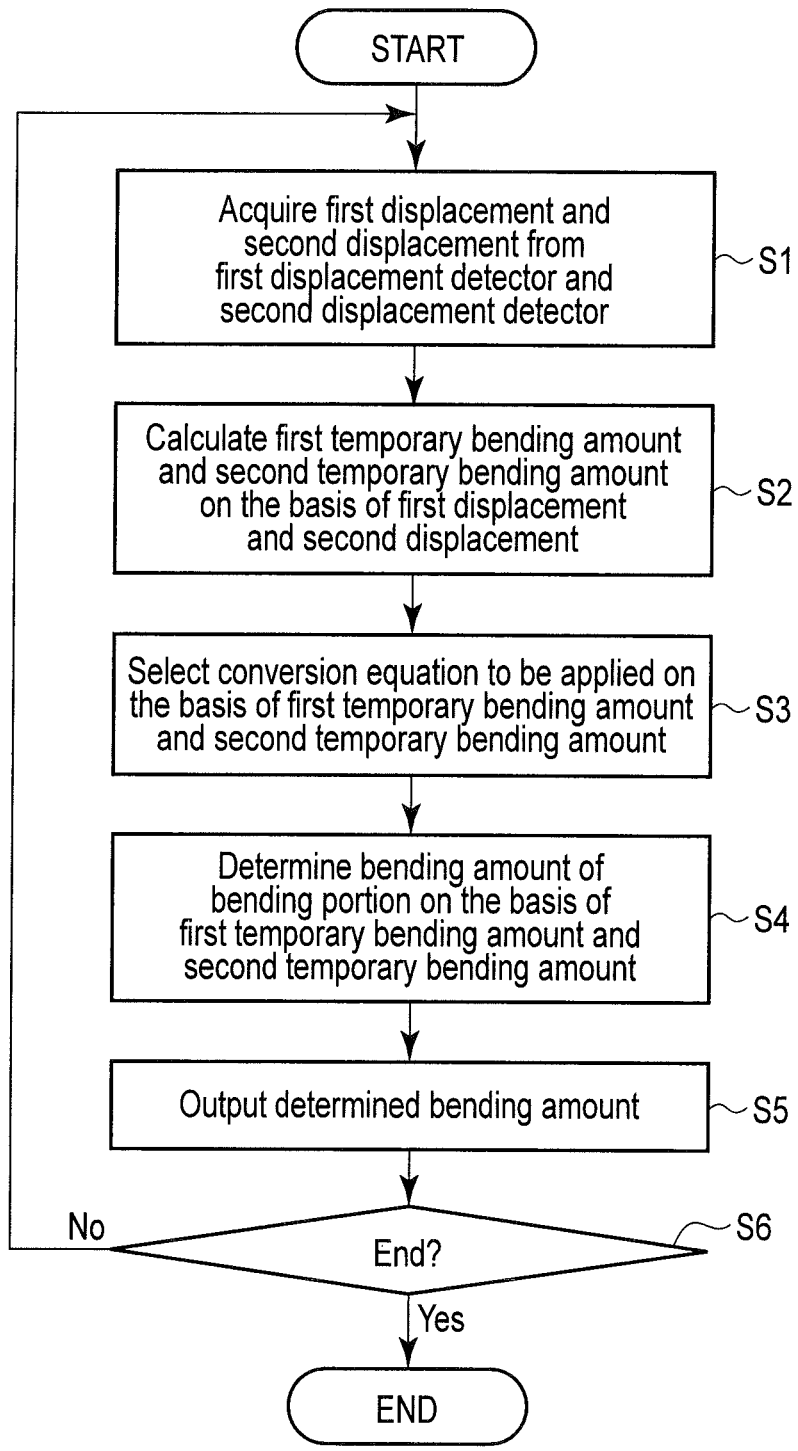
F I G. 7

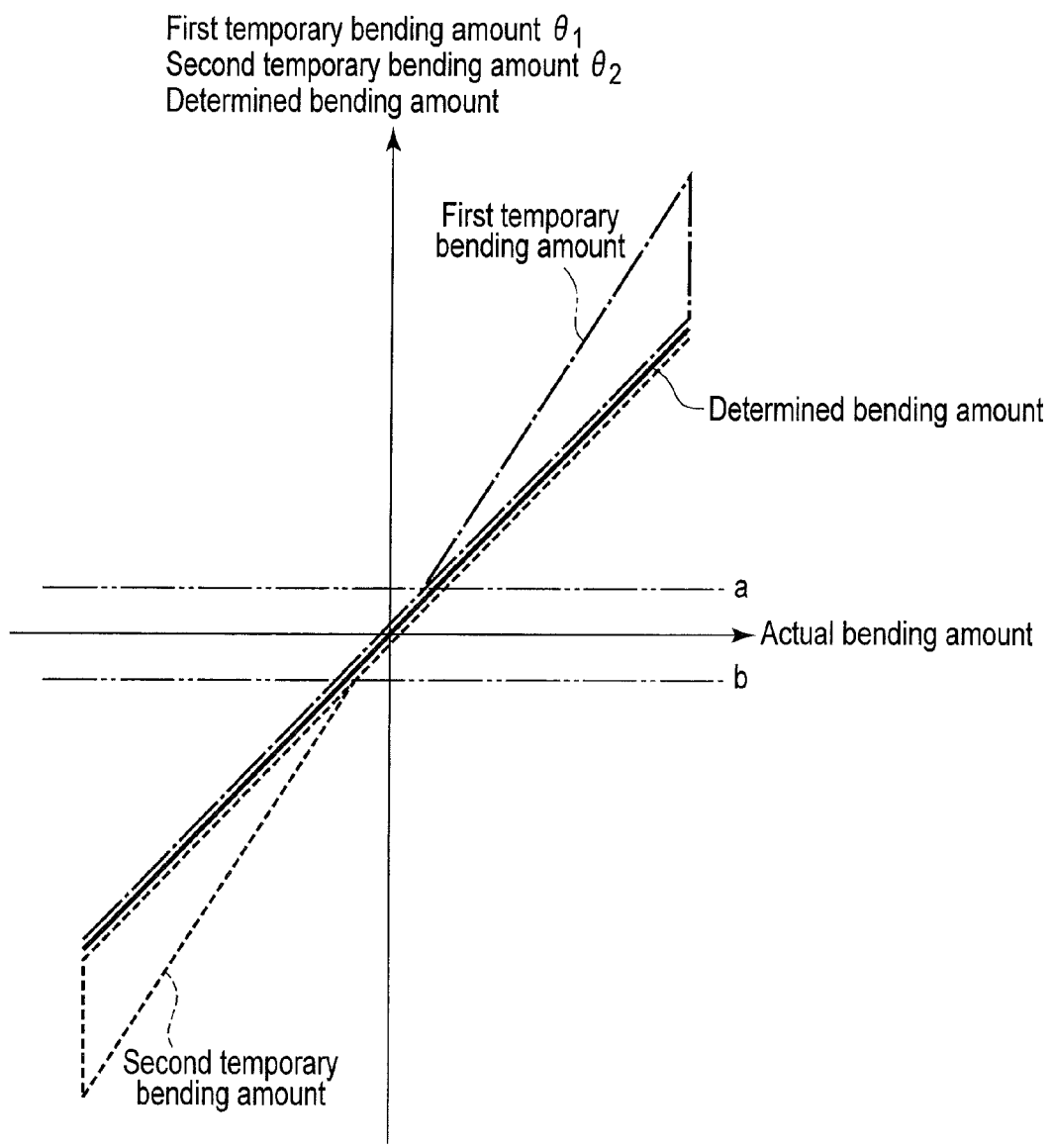
F I G. 9

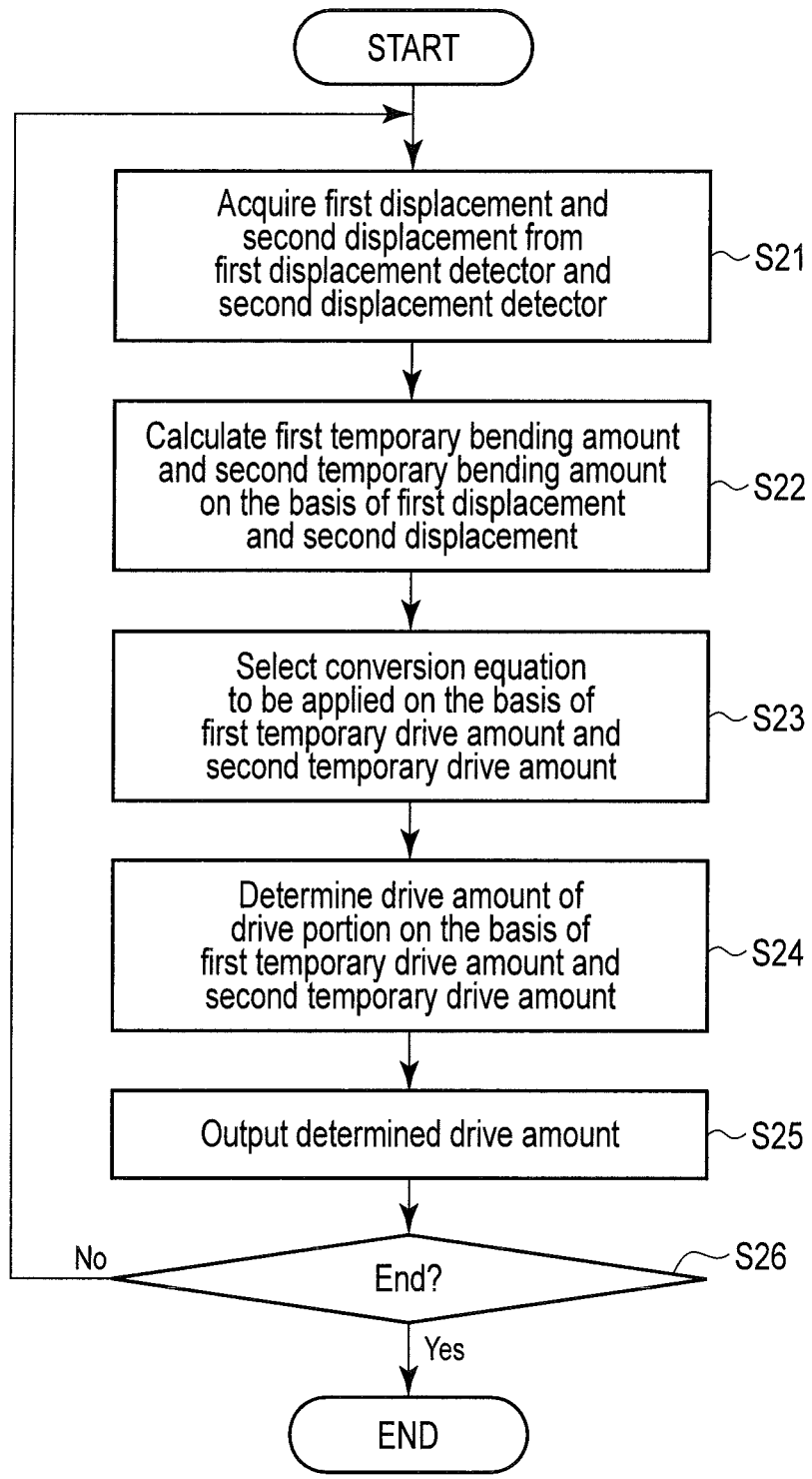
F I G. 11

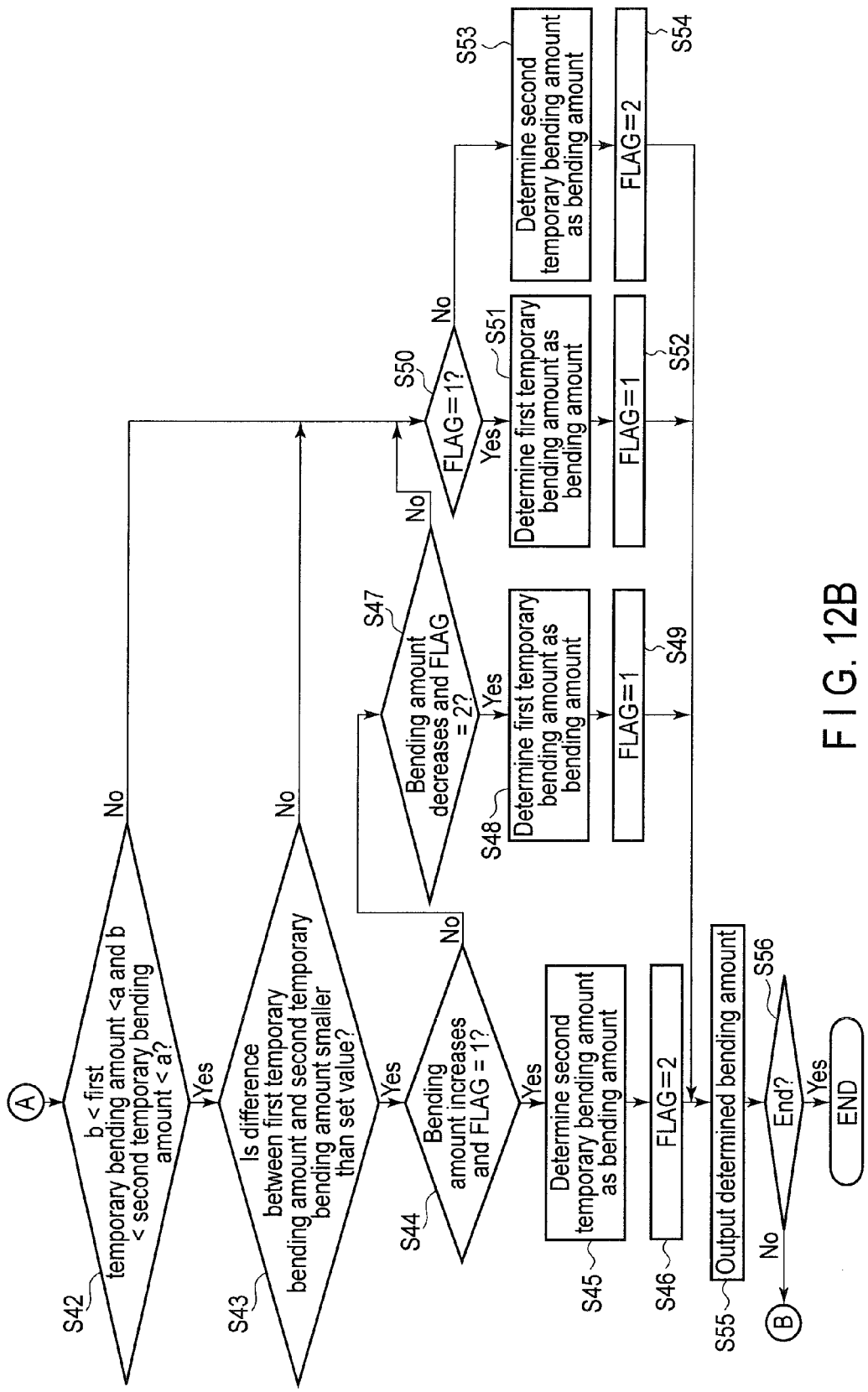
F I G. 12B

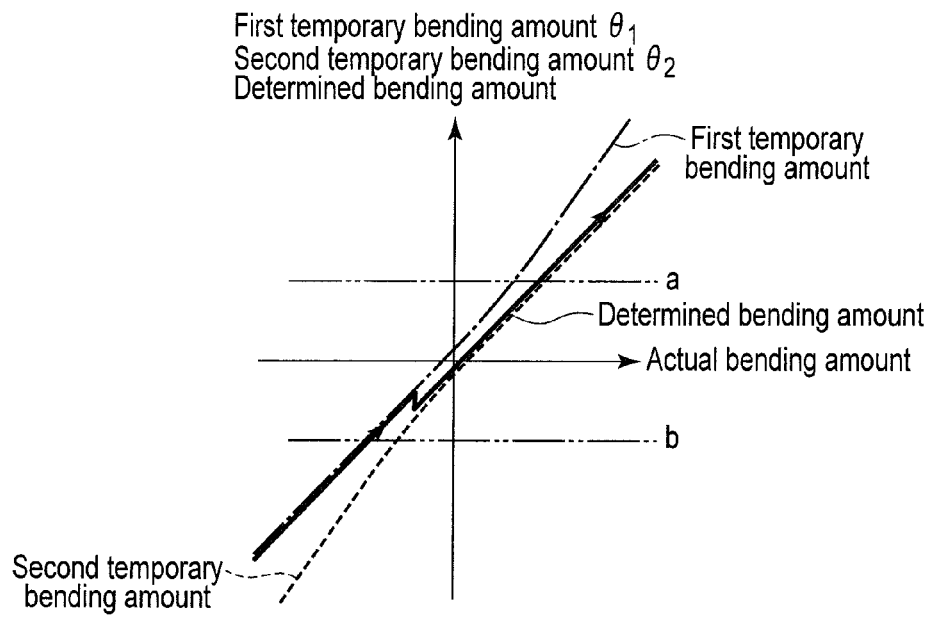
F I G. 13
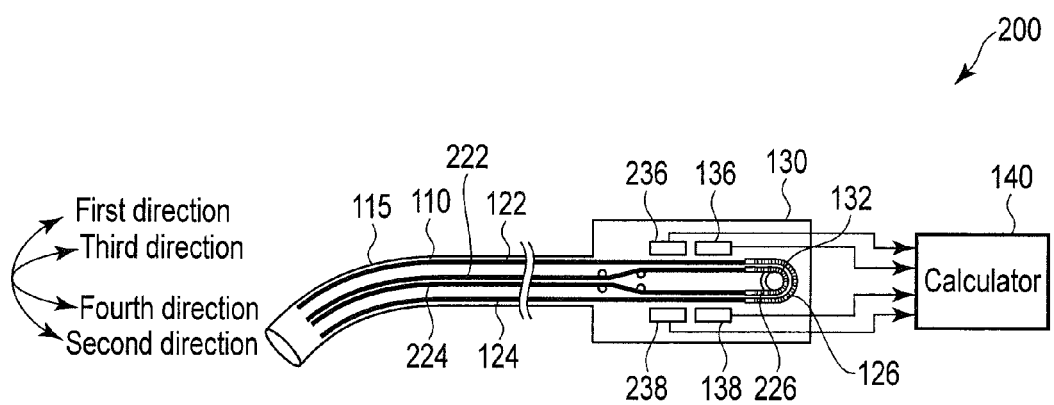
F I G. 14

BENDING OPERATION SYSTEM

CROSS-REFERENCE TO RELATED APPLICATIONS

This application is a Continuation application of PCT Application No. PCT/JP2012/076495, filed Oct. 12, 2012 and based upon and claiming the benefit of priority from prior Japanese Patent Application No. 2011-227113, filed Oct. 14, 2011, the entire contents of all of which are incorporated herein by reference.

BACKGROUND OF THE INVENTION

1. Field of the Invention

The present invention relates to a bending operation system.

2. Description of the Related Art

There is known, for example, a device having a tubular portion such as an endoscope or a manipulator which has a bending portion capable of a bending operation. In the endoscope or manipulator having such an operable bending portion, a wire is connected to the bending portion, and the bending portion is configured to be bent by the pulling of the wire. For example, a technique related to an endoscope is disclosed in Jpn. Pat. Appln. KOKAI Publication No. 61-087530, and this endoscope is provided with two wires each connected at one end to the vicinity of a bending portion. These two wires are displaced by a drum of an operation portion to which the other ends of the two wires are fixed, whereby the bending portion is bent.

In the endoscope or the manipulator disclosed in Jpn. Pat. Appln. KOKAI Publication No. 61-087530, it is possible that operation assist information is acquired in order to improve operability. For example, it is presumable to acquire an operation amount showing the shape of the bending portion or an operation amount of the operation portion as the operation assist information.

For example, one way of acquiring the operation assist information is to dispose an angle sensor in the bending portion, thereby measuring a bending amount of the bending portion. However, the bending portion is increased in size because of the angle sensor disposed in the bending portion and because of a wiring line for the angle sensor. For example, when it is intended for a tubular portion having this bending portion to be inserted into a narrow tube, the bending portion needs to be reduced in size. Conversely, however, disposing the angle sensor or the like in the bending portion is disadvantageous for size reduction of the tubular portion.

On the other hand, it is presumable that a displacement of the wire for driving the bending portion is acquired by, for example, an encoder, and operation assist information such as a bending amount of the bending portion is calculated on the basis of the displacement. However, the displacement of the wire and, for example, the bending amount of the bending portion are not in one-to-one correspondence sometimes. In this case, if a bending amount is calculated from the displacement of the wire on the basis of a function in which the displacement of the wire and the bending amount of the bending portion are in one-to-one correspondence, there is a possibility that the calculated bending amount may be different from an actual bending amount.

BRIEF SUMMARY OF THE INVENTION

An object of the present invention to provide a bending operation system in which accurate operation assist information can be calculated, reducing the size of a tubular portion.

To achieve the above described object, according to an aspect of the invention, a bending operation system includes an elongated tubular portion; a bending portion configured to be bendable within a predetermined movable range, the bending portion being included in the tubular portion; a first linear member, one end of which is connected to the tubular portion, the first linear member being configured to be displaced in a longitudinal direction to transmit power to bend the bending portion in a first direction; a second linear member, one end of which is connected to the tubular portion, the second linear member being configured to be displaced in a longitudinal direction to transmit power to bend the bending portion in a second direction which is opposite to the first direction; a drive portion configured to displace the first linear member and the second linear member; a first displacement detector configured to acquire a displacement of the first linear member as a first displacement; a second displacement detector configured to acquire a displacement of the second linear member as a second displacement; and a calculator configured to calculate operation assist information by use of one or both of the first displacement and the second displacement in accordance with a state of the bending portion.

According to the present invention, the operation assist information is calculated by use of one or both of the first displacement and the second displacement in accordance with the state of the bending portion, so that it is possible to provide a bending operation system in which accurate operation assist information can be calculated, reducing the size of a tubular portion.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 7 is a flowchart showing an example of processing by a calculator in the bending operation system according to the first embodiment;

FIG. 9 is a schematic diagram showing an example of the relation between the first temporary bending amount, the second temporary bending amount, and a bending amount determined by the calculator compared with an actual bending amount of the bending portion according to the first embodiment;

FIG. 11 is a flowchart showing an example of processing by the calculator in the bending operation system according to a modification of the first embodiment;

FIG. 12B is a flowchart showing the example of the processing by the calculator in the bending operation system according to the second embodiment following FIG. 12A;

FIG. 13 is a schematic diagram showing an example of the relation between a first temporary bending amount, a second temporary bending amount, and a bending amount determined by a calculator compared with an actual bending amount of the bending portion according to the second embodiment, and is an enlarged view of the vicinity of an origin; and FIG. 14 is a block diagram showing a configuration example of a bending operation system according to a third embodiment.

DETAILED DESCRIPTION OF THE INVENTION

First Embodiment

Figure 1:
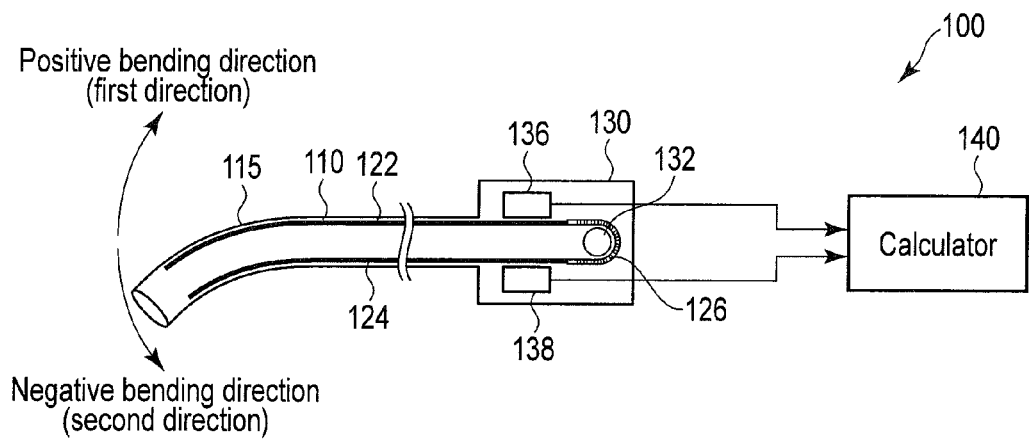
FIG. 1 is a block diagram showing a configuration example of a bending operation system according to a first embodiment.

A first embodiment of the present invention is described with reference to the drawings. A configuration example of a bending operation system 100 according to the first embodiment is shown in FIG. 1. The bending operation system 100 has an elongated tubular portion 110. A bending portion 115 is provided in the vicinity of one end of the tubular portion 110. The other end of the tubular portion 110 is connected to a grasp portion 130. A first wire 122 and a second wire 124 are inserted through the tubular portion 110. One end of each of the first wire 122 and the second wire 124 is connected to the vicinity of the bending portion 115. The other ends of the first wire 122 and the second wire 124 are coupled to each other by a chain 126 in the grasp portion 130.

A drive portion 132 is provided in the grasp portion 130. The drive portion 132 has an unshown sprocket, and a knob to rotate the sprocket. The teeth of the sprocket are engaged with the chain 126. The sprocket also rotates in response to the rotation of the knob, and power is transmitted to the chain 126. As a result, the first wire 122 and the second wire 124 that are coupled to the chain 126 are displaced together in a longitudinal direction, so that one wire is pulled and the other wire is played out. Since one end of the first wire 122 and one end of the second wire 124 are connected face to face to the vicinity of the bending portion 115, the bending portion 115 is bent in a first direction and a second direction by the displacement of the first wire 122 and the second wire 124 in the longitudinal direction. The first direction and the second direction are opposite to each other. Here, for the purpose of explanation, the bending of the bending portion 115 is defined so that the straight state of the bending portion 115 is 0 at a reference position, the upper side in FIG. 1 is a positive bending direction, and the lower side in FIG. 1 is a negative bending direction. The bending portion 115 is bent in the positive direction when the first wire 122 is pulled. The bending portion 115 is bent in the negative direction when the second wire 124 is pulled.

In the present embodiment, the drive portion 132 comprises the knob and the sprocket, and the knob is manually rotated by a user. However, the present invention is not limited to this, and the drive portion 132 may be configured so that the sprocket is driven by a motor or an actuator. The drive portion 132 may also be configured to have other driving means such as an actuator to displace the first wire 122 and the second wire 124. In this case, the first wire 122 and the second wire 124 do not need to be coupled by the chain 126, and the drive portion 132 has only to be configured so that power of the actuator is transmitted to the first wire and the second wire. Otherwise, the first wire and the second wire do not need to be coupled, and the drive portion 132 has only to be configured so that when one wire is pulled, the other wire can be freely displaced in accordance with the bending of the bending portion 115.

In the grasp portion 130, there are provided a first displacement detector 136 to detect a displacement of the first wire 122 in the longitudinal direction, and a second displacement detector 138 to detect a displacement of the second wire 124 in the longitudinal direction. The first displacement detector 136 and the second displacement detector 138 in the present embodiment are, for example, encoders. As will be described later, a first scale is fixed to the first wire 122, and a second scale is fixed to the second wire 124. The first displacement detector 136 detects a displacement of the first wire 122 by detecting a displacement of the first scale. The second displacement detector 138 detects a displacement of the second wire 124 by detecting a displacement of the second scale.

Each of the first displacement detector 136 and the second displacement detector 138 is connected to a calculator 140. The calculator 140 calculates a shape of the bending portion 115 on the basis of outputs of the first displacement detector 136 and the second displacement detector 138. Here, the shape of the bending portion 115 means, for example, an angle formed by tangent lines at both ends of the bending portion 115, i.e., an angle formed by a tangent line at a bending start position of the bending portion 115 and a tangent line at a bending end position thereof (hereinafter referred to as a bending amount), or a curvature of the bending portion 115. In the present embodiment, the bending amount is described as an example of the shape of the bending portion 115. Even when the curvature of the bending portion 115 or another expression representing the shape is used as the shape of the bending portion, a similar description applies in the following. It is to be noted that in the bending operation system 100 according to the present embodiment shown in FIG. 1, the calculator 140 is provided outside the grasp portion 130, but the calculator 140 may be provided inside the grasp portion 130. The calculator 140 outputs information on the shape of the bending portion 115.

Figure 2A:
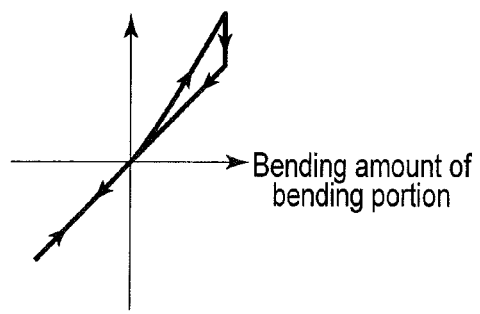
FIG. 2A is a schematic diagram illustrating the relation between the bending amount of a bending portion and the displacement of a first wire.
Figure 2B:
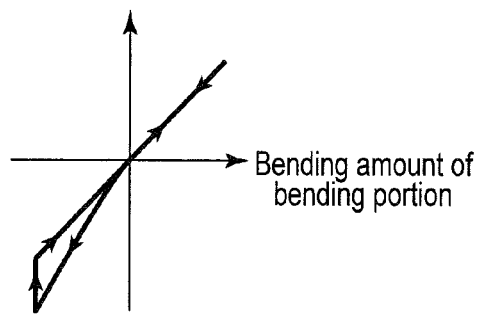
FIG. 2B is a schematic diagram illustrating the relation between the bending amount of the bending portion and the displacement of a second wire.

The relation between the displacement of the first wire 122 and the bending amount of the bending portion 115 is shown in FIG. 2A. Furthermore, the relation between the displacement of the second wire 124 and the bending amount of the bending portion 115 is shown in FIG. 2B. Here, as to the displacements of the first wire 122 and the second wire 124, a direction in which the first wire 122 is pulled is positive and a direction in which the second wire 124 is pulled is negative.

As shown in FIG. 2A, in the case where the displacement of the first wire 122 is positive, the relation between the displacement of the first wire 122 and the bending amount of the bending portion 115 is not matched between when the first wire 122 is pulled by the drive portion 132, i.e., when the displacement of the first wire 122 increases (when an absolute value of the displacement, i.e., a displacement amount increases) and when the second wire 124 is pulled, i.e., when the displacement of the first wire 122 decreases (when the displacement amount decreases). That is, a hysteresis phenomenon is observed. For example, even for the same displacement of the first wire 122, the bending amount of the bending portion 115 is larger (the absolute value of the bending amount is larger) when the second wire 124 is pulled than when the first wire 122 is pulled. On the other hand, as shown in FIG. 2A, when the displacement of the first wire 122 is negative, such hysteresis is not observed.

Similarly, as shown in FIG. 2B, in the case where the displacement of the second wire 124 is negative, the relation between the displacement of the second wire 124 and the bending amount of the bending portion 115 is not matched between when the second wire 124 is pulled by the drive portion 132, i.e., when the displacement of the second wire 124 decreases (when the displacement amount increases) and when the first wire 122 is pulled, i.e., when the displacement of the second wire 124 increases (when the displacement amount decreases). That is, the hysteresis phenomenon is observed. For example, even for the same displacement of the second wire 124, the bending amount of the bending portion 115 is smaller (the absolute value of the bending amount is larger) when the first wire 122 is pulled than when the second wire 124 is pulled. On the other hand, as shown in FIG. 2B, when the displacement of the second wire 124 is positive, such hysteresis is not observed.

When the bending amount of the bending portion 115 is to be determined by using only one of the displacement of the first wire 122 and the displacement of the second wire 124 in this manner, there is a possibility that the above hysteresis causes an error in the bending amount to be determined. Thus, in the present embodiment, the calculator 140 determines the bending amount of the bending portion 115 by use of both of the displacement of the first wire 122 and the displacement of the second wire 124. More specifically, the calculator 140 determines the bending amount of the bending portion 115 on the basis of the displacement of the second wire 124 when the bending amount of the bending portion 115 is positive, and the calculator determines the bending amount of the bending portion 115 on the basis of the displacement of the first wire 122 when the bending amount of the bending portion 115 is negative.

Figure 3A:
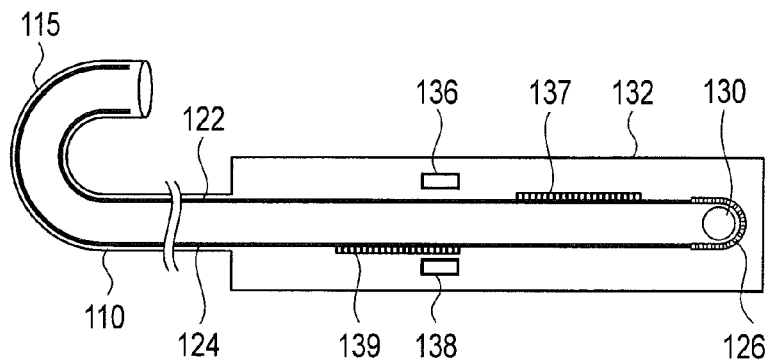
FIG. 3A is a diagram illustrating a configuration example of the bending operation system according to the first embodiment, particularly a configuration example of a displacement detector, and showing that the bending portion is bent in a positive bending direction.
Figure 3B:
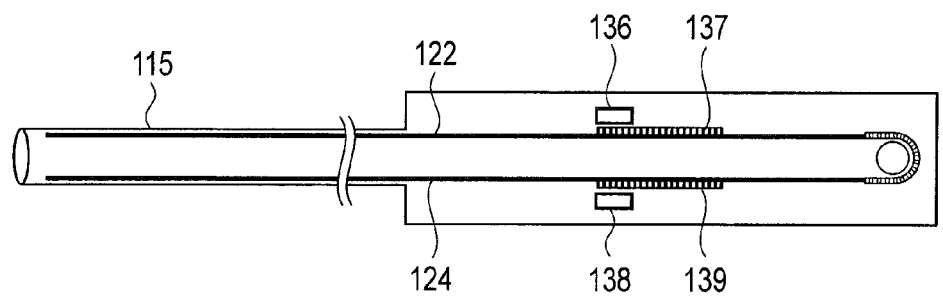
FIG. 3B is a diagram illustrating a configuration example of the bending operation system according to the first embodiment, particularly a configuration example of the displacement detector, and showing that the bending portion is straight.
Figure 3C:
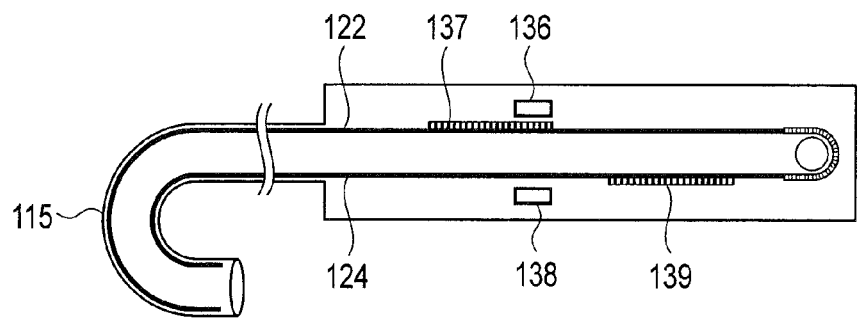
FIG. 3C is a diagram illustrating a configuration example of the bending operation system according to the first embodiment, particularly a configuration example of the displacement detector, and showing that the bending portion is bent in a negative bending direction.

A configuration example concerning the first displacement detector 136 and the second displacement detector 138 of the present embodiment is shown in FIG. 3A, FIG. 3B and FIG. 3C. FIG. 3A schematically shows that the bending portion 115 is bent in the positive bending direction, FIG. 3B schematically shows that the bending portion 115 is straight, and FIG. 3C schematically shows that the bending portion 115 is bent in the negative bending direction. As shown in these drawings, a first scale 137 as an encoder scale for the first displacement detector 136 is fixed to the first wire 122, and a second scale 139 as an encoder scale for the second displacement detector 138 is fixed to the second wire 124.

In the present embodiment, the first scale 137 and the second scale 139 are disposed closer to the side of the chain 126 than the first displacement detector 136 and the second displacement detector, respectively. That is, as shown in FIG. 3A, when the first wire 122 is pulled to bend the bending portion 115 in the positive bending direction, the second scale 139 moves at a position facing the second displacement detector 138. Therefore, the second displacement detector 138 measures the displacement of the second wire 124 mainly when the first wire 122 is pulled to bend the bending portion 115 in the positive bending direction. Furthermore, as shown in FIG. 3C, when the second wire 124 is pulled to bend the bending portion 115 in the negative bending direction, the first scale 137 moves at a position facing the first displacement detector 136. Therefore, the first displacement detector 136 measures the displacement of the first wire 122 mainly when the second wire 124 is pulled to bend the bending portion 115 in the negative bending direction.

Figure 4:
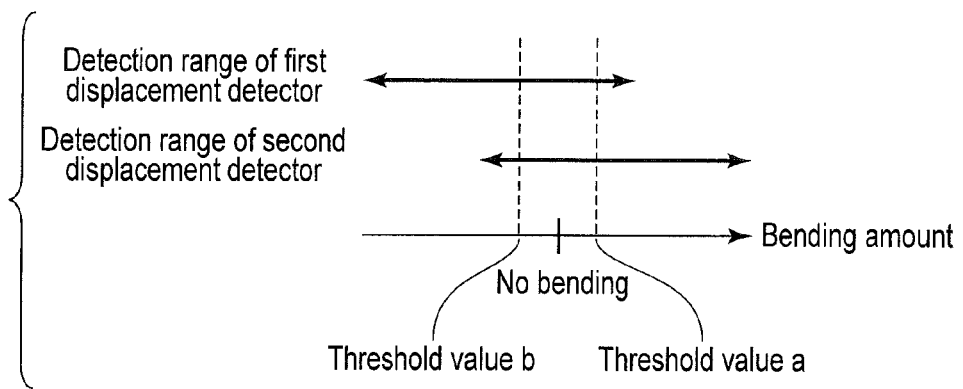
FIG. 4 is a diagram illustrating an example of the relation between the bending amount of the bending portion and a detection range of the displacement detector.

FIG. 4 illustrates the relation between the bending amount of the bending portion 115 and a detection range of the first displacement detector 136 and the first scale 137, and the relation between the bending amount of the bending portion 115 and a detection range of the second displacement detector 138 and the second scale 139. The first displacement detector 136 and the first scale 137 detect the bending amount in all ranges in the negative bending direction of the bending portion 115 and a range including an after-mentioned first threshold value a of the positive bending direction from a state where the bending portion 115 is not bent. On the other hand, the second displacement detector 138 and the second scale 139 detect the bending amount in all ranges of the positive bending direction of the bending portion 115 and a range including an after-mentioned second threshold value b of the negative bending direction from the state where the bending portion 115 is not bent. Here, the first threshold value a is a>0 and the second threshold value b is b<0. As described above, the detection range of the first displacement detector 136 and the first scale 137 partially overlaps with the detection range of the second displacement detector 138 and the second scale 139.

Figure 5A:
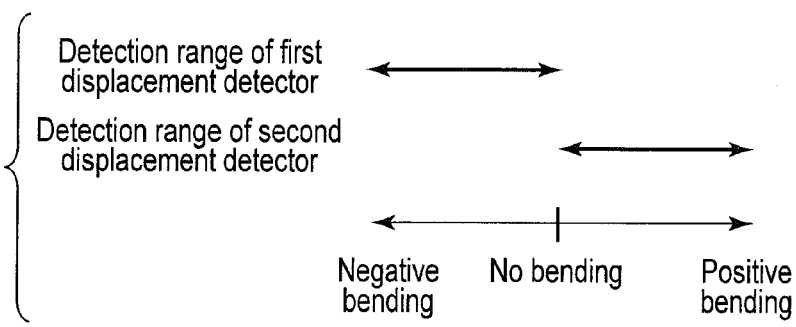
FIG. 5A is a diagram illustrating another example of the relation between the bending amount of the bending portion and a detection range of the displacement detector.
Figure 5B:
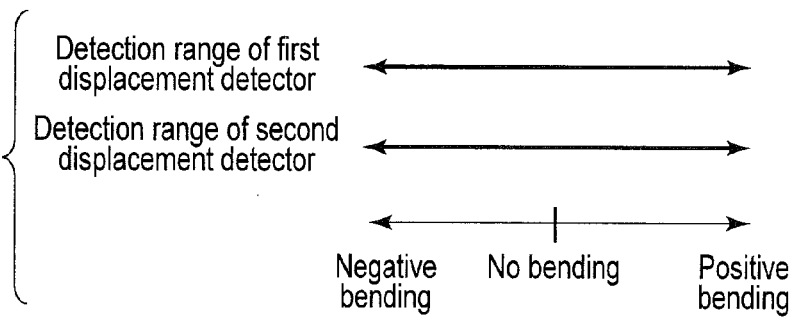
FIG. 5B is a diagram illustrating yet another example of the relation between the bending amount of the bending portion and the detection range of the displacement detector.
Figure 6A:
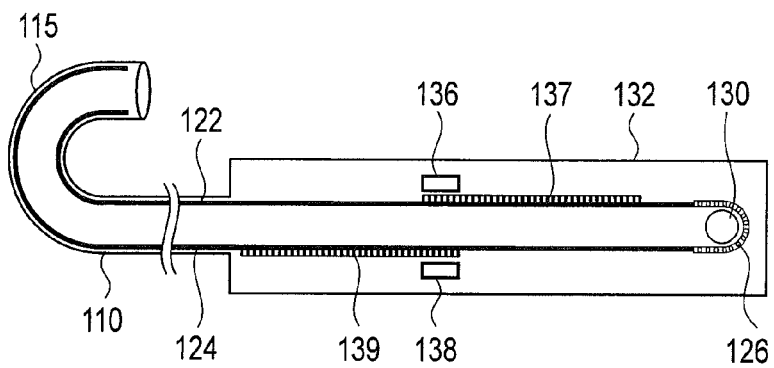
FIG. 6A is a diagram illustrating a configuration example of the bending operation system, particularly another configuration example of the displacement detector, and showing that the bending portion is bent in the positive bending direction.
Figure 6B:
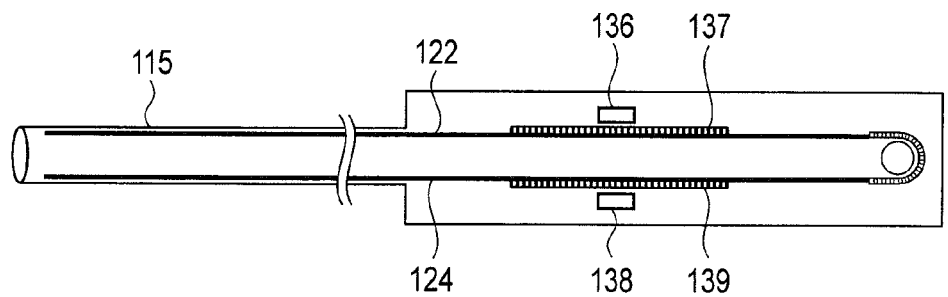
FIG. 6B is a diagram illustrating a configuration example of the bending operation system, particularly another configuration example of the displacement detector, and showing that the bending portion is straight.
Figure 6C:
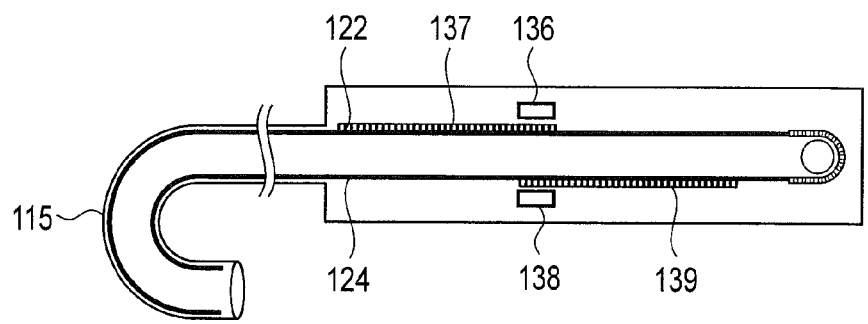
FIG. 6C is a diagram illustrating a configuration example of the bending operation system, and in particular, a configuration example of the displacement detector, and showing that the bending portion is bent in the negative bending direction.

It is to be noted that as shown in FIG. 5A, it can be set that the detection range of the first displacement detector 136 and the first scale 137 does not overlap with the detection range of the second displacement detector 138 and the second scale 139. Furthermore, as shown in FIG. 5B, both of the detection range of the first displacement detector 136 and the first scale 137 and the detection range of the second displacement detector 138 and the second scale 139 can be overall bending range of the bending portion 115. In this case, the first scale 137 and the second scale 139 are disposed as shown in FIG. 6A, FIG. 6B and FIG. 6C.

A space around the first wire 122 and the second wire 124 in the grasp portion 130 is limited, and hence in some cases, there is a possibility that the first scale 137 and the second scale 139 interfere with another constituent object and the elongated first scale 137 and second scale 139 cannot be disposed. Therefore, as described with reference to FIG. 3A, FIG. 3B, FIG. 3C and FIG. 4, the detection range of the first displacement detector 136 and the first scale 137 and the detection range of the second displacement detector 138 and the second scale 139 are regulated, so that the first scale 137 and the second scale 139 can be shortened, which facilitates the disposing of the scales. As a result, a degree of freedom in design of the bending operation system 100 is enhanced.

Next, an operation of the bending operation system 100 is described. The user grasps the grasp portion 130 and operates the drive portion 132 to bend the bending portion 115 of the tubular portion 110 to a desirable angle. That is, the user rotates the knob of the drive portion 132. When this knob rotates to rotate the sprocket, the chain 126 engaged with the sprocket is displaced. In response to the displacement of the chain 126, the first wire 122 and the second wire 124 are displaced. As a result, the bending portion 115 of the tubular portion 110 is bent.

At this time, the first scale 137 fixed to the first wire 122 and the second scale 139 fixed to the second wire 124 are displaced. The first displacement detector 136 converts the displacement of the first scale 137 into an electric signal to output the signal to the calculator 140. Here, the displacement of the first scale 137, i.e., the displacement of the first wire 122 is referred to as a first displacement Enc1. Similarly, the second displacement detector 138 converts the displacement of the second scale 139 into an electric signal to output the signal to the calculator 140. Here, the displacement of the second scale 139, i.e., the displacement of the second wire 124 is referred to as a second displacement Enc2.

The processing in the calculator 140 is described with reference to a flowchart shown in FIG. 7. In step S1, the calculator 140 acquires the first displacement Enc1 from the first displacement detector 136 and acquires the second displacement Enc2 from the second displacement detector 138.

In step S2, the calculator 140 calculates a first temporary bending amount $\theta_1$ as a temporary value of the bending amount of the bending portion 115 in accordance with Equation (1) described in the following on the basis of the first displacement Enc1.

$$\theta_1 = \alpha 1 \times Enc1 \quad (1)$$

Similarly, the calculator 140 calculates a second temporary bending amount $\theta_2$ as a temporary value of the bending amount of the bending portion 115 in accordance with Equation (2) described in the following on the basis of the second displacement Enc2.

$$\theta_2 = \alpha 2 \times Enc2 \quad (2)$$

Here, $\alpha 1$ and $\alpha 2$ are predetermined constants.

The constant $\alpha 1$ is beforehand determined on the basis of the obtained relation between the displacement of the first wire 122 and the bending amount of the bending portion 115 when the bending portion 115 is bent in the negative bending direction. Similarly, the constant $\alpha 2$ is beforehand determined on the basis of the obtained relation between the displacement of the second wire 124 and the bending amount of the bending portion 115 when the bending portion 115 is bent in the positive bending direction. It is to be noted that the constant $\alpha 1$ is usually substantially equal to the constant $\alpha 2$, and hence one of the constant $\alpha 1$ and the constant $\alpha 2$ may be obtained and the obtained value may be used as both of the constant $\alpha 1$ and the constant $\alpha 2$. It is to be noted that in Equations (1) and (2) described above, the relation between the bending amount of the bending portion 115 and the first temporary bending amount $\theta_1$ or the second temporary bending amount $\theta_2$ is a simple proportional relation, but the present embodiment is not limited to this, and any equation such as a high order equation may be used as long as the equation represents these relations sufficiently well.

Furthermore, instead of using Equations (1) and (2) described above, the relation between the displacement of the first wire 122 and the bending amount of the bending portion 115 when the bending portion 115 is bent in the negative bending direction and the relation between the displacement of the second wire 124 and the bending amount of the bending portion 115 when the bending portion 115 is bent in the positive bending direction may beforehand be obtained, and these relations may be prepared in a table. In this case, on the basis of this table, the calculator 140 determines the first temporary bending amount $\theta_1$ from the first displacement Enc1 and determines the second temporary bending amount $\theta_2$ from the second displacement Enc2.

Figure 8:
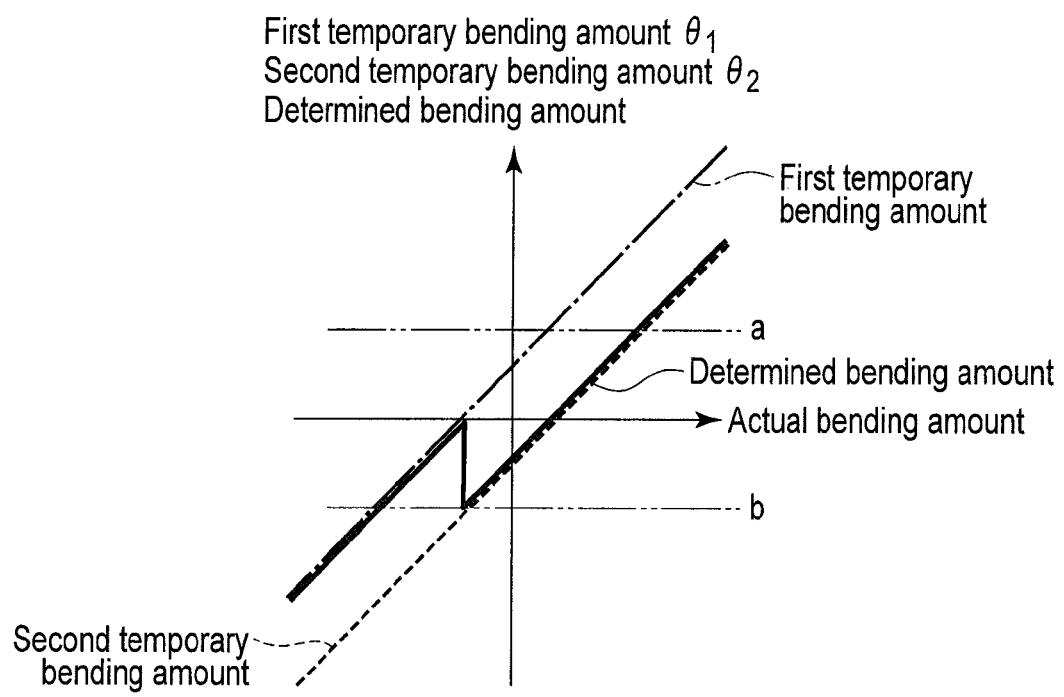
FIG. 8 is a schematic diagram illustrating an example of the relation between a first temporary bending amount, a second temporary bending amount, and a bending amount determined by the calculator compared with an actual bending amount of the bending portion when the first embodiment is not applied, and is an enlarged view of the vicinity of an origin.

Here, a method in which the first temporary bending amount $\theta_1$ is determined as a final bending amount when the bending portion is bent in the negative bending direction and the second temporary bending amount $\theta_2$ is determined as a final bending amount when the bending portion is bent in the positive bending direction may be applied, as long as the first temporary bending amount $\theta_1$ and the second temporary bending amount $\theta_2$ are matched or have a difference therebetween to such an extent that there are no problems during use, when the actual bending amount of the bending portion 115 is 0 (straight). However, as shown in FIG. 8, when the actual bending amount of the bending portion 115 is 0, the first temporary bending amount $\theta_1$ and the second temporary bending amount $\theta_2$ are not simultaneously necessarily 0 due to a structure of the tubular portion 110 or the grasp portion 130, and a slight deviation is generated in the amounts sometimes. At this time, if the selection of the first temporary bending amount $\theta_1$ or the second temporary bending amount $\theta_2$ is simply changed by determining whether or not the bending amount is 0 or more as a condition to acquire the final bending amount, a value of the bending amount disadvantageously changes rapidly or changes opposite to the actual bending direction sometimes. Therefore, the user has a feeling of incongruity between the amount of the rotated operation knob and the change of the calculated bending amount. Therefore, the calculation is performed in accordance with the next algorithm so that the value of the calculated bending amount does not change rapidly or does not change opposite to the actual bending direction.

In step S3, on the basis of the first temporary bending amount $\theta_1$ and the second temporary bending amount $\theta_2$, the calculator 140 selects a conversion equation (a processing method of the value) for calculating the bending amount of the bending portion 115 with reference to the relation shown in Table 1 described in the following.

TABLE 1

| First temporary bending amount | Second temporary bending amount | Value processing method |
|---|---|---|
| $\theta_1 \geq a$ | $\theta_2 \geq a$ | Use value of $\theta_2$ |
| $b < \theta_1 < a$ | $\theta_2 \geq a$ | |
| $\theta_1 > a$ | $b < \theta_2 < a$ | Use weighted average value |
| $b < \theta_1 < a$ | $b < \theta_2 < a$ | |
| $b < \theta_1 < a$ | $\theta_2 < b$ | |
| $\theta_1 \leq b$ | $b < \theta_2 < a$ | Use value of $\theta_1$ |
| $\theta_1 \leq b$ | $\theta_2 \leq b$ | |

In step S4, the calculator 140 determines the bending amount of the bending portion 115 in accordance with the conversion equation selected in step S3 on the basis of the first temporary bending amount $\theta_1$ and the second temporary bending amount $\theta_2$. That is, as shown in Table 1, when $\theta_1 \geq a$ and $\theta_2 \geq a$ or when $b < \theta_1 < a$ and $\theta_2 \geq a$, the second temporary bending amount $\theta_2$ is determined as the bending amount of the bending portion 115. Furthermore, when $\theta_1 > a$ and $b < \theta_2 < a$, when $b < \theta_1 < a$ and $b < \theta_2 < a$, or when $b < \theta_1 < a$ and $\theta_2 < b$, a weighted average using the first temporary bending amount $\theta_1$ and the second temporary bending amount $\theta_2$ is determined as the bending amount of the bending portion 115. Furthermore, when $\theta_1 \leq b$ and $b < \theta_2 < a$ or when $\theta_1 \leq b$ and $\theta_2 \leq b$, the first temporary bending amount $\theta_1$ is determined as the bending amount of the bending portion 115.

Here, as an equation to obtain the weighted average indicating a bending amount $\theta$ of the bending portion 115, for example, Equation (3) described in the following is used.

$$\theta = f(\theta_1, \theta_2) \times \theta_1 + (1 - f(\theta_1, \theta_2)) \times \theta_2 \qquad (3)$$

As a specific example of Equation (3) described above, Equation (4) described in the following can be used.

$$\theta = \frac{a - \theta_2}{a - \theta_2 + \theta_1 - b} \times \theta_1 + \frac{\theta_1 - b}{a - \theta_2 + \theta_1 - b} \times \theta_2 \qquad (4)$$

In the above description, the first temporary bending amount $\theta_1$ and the second temporary bending amount $\theta_2$ are used in a function concerned with a weight, but even if the first displacement Enc1 and the second displacement Enc2 are used, a similar description applies. In this case, Equation (3) described above is represented by, for example, Equation (5) described in the following.

$$\theta = f(Enc1, Enc2) \times \theta_1 + (1 - f(Enc1, Enc2)) \times \theta_2 \qquad (5)$$

Furthermore, by a method of calculating the bending amount $\theta$ on the basis of a weighted average of the first displacement Enc1 and the second displacement Enc2 using a weight function concerned with the first displacement End and the second displacement Enc2, the bending amount may be obtained in accordance with Equations (6) and (7) described in the following. That is, first, a weighted average value Enc of the first displacement End and the second displacement Enc2 may be obtained, and the bending amount $\theta$ may be obtained from the weighted average value Enc by use of a function h.

$$Enc = f(Enc1, Enc2) \times Enc1 + (1 - f(Enc1, Enc2)) \times Enc2 \qquad (6)$$

$$0 = h(Enc) \qquad (7)$$

Figure 10:
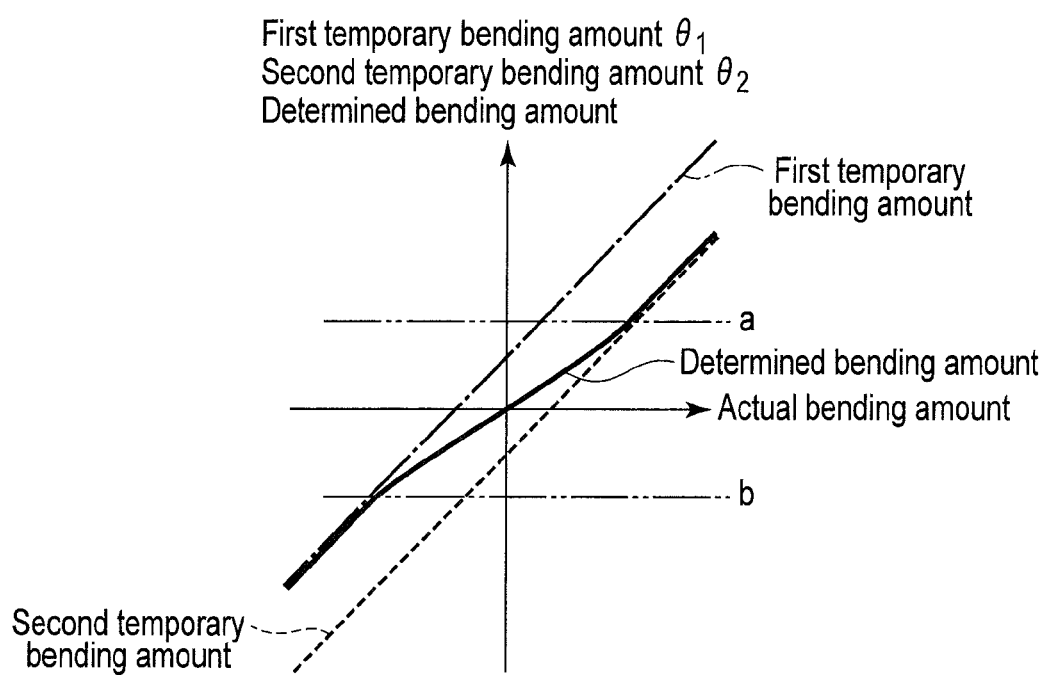
FIG. 10 is a schematic diagram showing an example of the relation between the first temporary bending amount, the second temporary bending amount, and a bending amount determined by the calculator compared with an actual bending amount of the bending portion according to the first embodiment, and is an enlarged view of the vicinity of an origin.

Schematic diagrams showing the relation between the first temporary bending amount $\theta_1$, the second temporary bending amount $\theta_2$ and the bending amount of the bending portion 115 which is determined by the calculator 140 compared with the actual bending amount of the bending portion 115 are shown in FIG. 9 and FIG. 10. FIG. 10 is a partially enlarged view of the vicinity of an origin. In FIG. 9 and FIG. 10, a dashed-dotted line indicates the first temporary bending amount $\theta_1$, a broken line indicates the second temporary bending amount $\theta_2$, and a solid line indicates the bending amount of the bending portion 115 which is determined by the calculator 140. It is to be noted that in FIG. 9 and FIG. 10, actually completely matching lines are slightly shifted for ease of understanding.

As shown in these drawings, generally, when the bending portion 115 is bent in the negative bending direction, the calculator 140 determines the first temporary bending amount $\theta_1$ on the basis of the output of the first displacement detector 136 as the bending amount of the bending portion 115. When the bending portion 115 is bent in the positive bending direction, the calculator 140 determines the second temporary bending amount $\theta_2$ on the basis of the output of the second displacement detector 138 as the bending amount of the bending portion 115. Between the first threshold value a and the second threshold value b, the calculator 140 calculates the weighted average on the basis of the first temporary bending amount $\theta_1$ and the second temporary bending amount $\theta_2$ to determine the bending amount of the bending portion 115.

In step S5, the calculator 140 outputs the determined bending amount of the bending portion 115. On the basis of the output bending amount, the bending operation system 100 or another device may display, for example, the value of the determined bending amount or a diagram or a graph showing the bending amount on a display or the like, to present the bending amount to the user. Furthermore, on the basis of the output bending amount, the bending operation system 100 or the other device may use the output bending amount in any form of control. In step S6, the calculator 140 determines whether or not the end of the calculation processing of the bending amount is instructed. When the end is not instructed, the processing returns to the step S1. On the other hand, when the end is instructed, a series of processing ends.

In the present embodiment, the bending amount of the bending portion 115 is determined as described above, so that the bending amount can accurately be determined. That is, when the bending amount of the bending portion 115 is calculated by using only one of the first displacement Enc1 of the first wire 122 and the second displacement Enc2 of the second wire 124, for example, the bending amount and the displacement of the first wire 122 or the second wire 124 are not in one-to-one correspondence due to the hysteresis, and hence the bending amount cannot be calculated or the error included in the calculated bending amount is large. In contrast to the above, in the present embodiment, the bending amount of the bending portion 115 can accurately be determined by using both of the first displacement End and the second displacement Enc2. By the accurate detection of the bending amount, for example, an operability of the bending portion 115 by the user can be enhanced, or a quality of the control of the system can be enhanced.

Furthermore, the weighted average on the basis of the first temporary bending amount $\theta_1$ and the second temporary bending amount $\theta_2$ is calculated in the state where the bending amount of the bending portion 115 is between the first threshold value a and the second threshold value b, so that a deviation between the first temporary bending amount $\theta_1$ and the second temporary bending amount $\theta_2$ can smoothly be connected. That is, for example, it is simply presumed that when the first temporary bending amount $\theta_1$ is negative, the first temporary bending amount $\theta_1$ is acquired as the bending amount of the bending portion 115, and when the first temporary bending amount $\theta_1$ is positive, the second temporary bending amount $\theta_2$ is acquired as the bending amount of the bending portion 115. In this case, the actual bending amount of the bending portion 115 and the bending amount determined by the calculator 140 have, for example, such a relation as shown in FIG. 8. In this case, when the use of the first temporary bending amount $\theta_1$ and the use of the second temporary bending amount $\theta_2$ are switched, for example, the value of the bending amount determined by the calculator 140 discontinuously decreases irrespective of the continuous increase in the actual bending amount, i.e., a reverse phenomenon discontinuously takes place. Such discontinuity or the reverse phenomenon of the change of the bending amount gives a feeling of incongruity to the user, for example, when the bending amount is presented to the user. In contrast, in the present embodiment, the bending amount determined by the calculator 140 can smoothly and continuously be changed as described above, and hence no feeling of incongruity is given to the user.

It is to be noted that when the actual bending amount of the bending portion 115 is 0 (when the bending portion 115 is straight) and when the first temporary bending amount $\theta_1$ and the second temporary bending amount $\theta_2$ are matched or when a difference is only present therebetween to such an extent that there are no problems during the use, another method of determining the bending amount can be used in which, for example, when the bending amount is negative, the first temporary bending amount $\theta_1$ is determined as the bending amount of the bending portion 115, and when the bending amount is positive, the second temporary bending amount $\theta_2$ is determined as the bending amount of the bending portion 115. In this case, as shown in FIG. 5A, the first scale 137 may be designed to have such a length that the scale is capable of measuring the bending amount only in a range where the bending amount is negative, and the second scale 139 may be designed to have such a length that the scale is capable of measuring the bending amount only in a range where the bending amount is positive. As a result, the first scale 137 and the second scale 139 can further be shortened, and the degree of freedom in design of the bending operation system 100 is further enhanced.

Furthermore, each of Equation (3) to Equation (7) described above in the present embodiment is, needless to say, an example, and another function may be used. For example, another continuous function, which sufficiently demonstrates the relation between the first temporary bending amount $\theta_1$ or the second temporary bending amount $\theta_2$ and the actual bending amount of the bending portion 115, and which includes a value between the first threshold value a and the second threshold value b, can be used.

In the present embodiment, the first displacement detector 136 and the second displacement detector 138 are disposed in the grasp portion 130, so that the displacements of the first wire 122 and the second wire 124 can be detected, reducing a size of a tip side of the tubular portion 110 provided with the bending portion 115. Therefore, the tubular portion 110 provided with the bending portion 115 of the present embodiment can realize a tubular portion which can be inserted into a narrow space such as the inside of a body cavity or a tube.

Furthermore, in the present embodiment, as shown in FIG. 3A, FIG. 3B, FIG. 3C and FIG. 4, the first scale 137 and the second scale 139 are disposed only in a range where the first wire 122 and the second wire 124 move as required for the calculator 140 to determine the bending amount. In consequence, the first scale 137 and the second scale 139 can be shortened and the degree of freedom in design of the bending operation system 100 is enhanced.

In the present embodiment, the first wire 122 and the second wire 124 are coupled to each other by the chain 126, and the first wire 122 and the second wire 124 are displaced together in the longitudinal direction. In consequence, the first wire 122 and the second wire 124 do not need to be separately driven, respectively. In the present embodiment, when the sprocket engaged with the chain 126 is simply rotated by using the knob, the first wire 122 and the second wire 124 can be displaced, i.e., the bending portion 115 can be bent. Furthermore, when the wires are driven by a motor or the like instead of the user rotating the knob, the first wire 122 and the second wire 124 do not need to be provided with motors, respectively, and the present system can be realized simply by providing one motor in the sprocket.

As described above, for example, the tubular portion 110 functions as an elongated tubular portion. For example, the bending portion 115 functions as a bending portion which is bendable within a predetermined movable range and is included in the tubular portion. For example, the first wire 122 functions as a first linear member which has one end connected to the tubular portion and is displaced in a longitudinal direction, thereby transmitting power to bend the bending portion in a first direction. For example, the second wire 124 functions as a second linear member which has one end connected to the tubular portion and is displaced in the longitudinal direction, thereby transmitting power to bend the bending portion in a second direction opposite to the first direction. For example, the drive portion 132 functions as a drive portion which displaces the first linear member and the second linear member. For example, the first displacement detector 136 functions as a first displacement detector which acquires a displacement of the first linear member as a first displacement. For example, the second displacement detector 138 functions as a second displacement detector which acquires a displacement of the second linear member as a second displacement. For example, the calculator 140 functions as a calculator which calculates operation assist information by use of one or both of the first displacement and the second displacement in accordance with a state of the bending portion. For example, the bending amount functions as the operation assist information. For example, a position where the bending portion is straight functions as a reference position. For example, the first threshold value a functions as a first bending threshold value indicating a state where the bending portion is bent as much as a predetermined amount from the reference position in the first direction and, for example, the second bending threshold value b functions as a second bending threshold value indicating a state where the bending portion is bent as much as a predetermined amount from the reference position in the second direction. For example, the chain 126 functions as a coupling member coupling the other end of the first linear member to the other end of the second linear member.

In the present embodiment, examples of the linear member include the first wire 122 and the second wire 124, but the present invention is not limited to the examples. A material is not limited to a metal, and may be a high molecular compound such as a resin, and any material may be used as long as the material is a linear member which moves in the longitudinal direction to transmit the power. Furthermore, in the present embodiment, an example of the displacement detector is an encoder, but the present invention is not limited to this example. Any detector may be used, as long as the displacements of the first wire 122 and the second wire 124 can be detected.

In the present embodiment, the state where the tubular portion 110 is straight is the reference position. However, as long as the relation between the actual bending amount of the bending portion 115 and the displacement of the first wire 122 is symmetric to the relation between the actual bending amount of the bending portion 115 and the displacement of the second wire 124 via the reference position, a configuration similar to the above configuration can be obtained even when the reference position is a state where the tubular portion 110 is bent.

[Modification of First Embodiment]

A modification of the first embodiment will be described. Here, a different aspect from the first embodiment will be described, the same parts are denoted with the same reference symbols, and descriptions of such parts are omitted. In the first embodiment, the calculator 140 outputs the bending amount of the bending portion 115. In contrast to the above, in the present modification, a calculator 140 outputs a drive amount of a drive portion 132. Here, in the present modification, the drive amount is an operation amount of a knob operated by a user.

In the present modification, similarly to the relation between the first displacement Enc1 and the bending amount of the bending portion 115 in the first embodiment, the relation between a first displacement Enc1 of a first wire 122 and the drive amount of the knob is beforehand acquired. Similarly, the relation between a second displacement Enc2 of a second wire 124 and the drive amount of the knob is beforehand acquired. The calculator 140 can obtain the drive amount of the knob on the basis of the first displacement Enc1 and the second displacement Enc2 by utilizing these relations.

An example of processing of the calculator 140 in the present modification is described with reference to a flowchart shown in FIG. 11. In step S21, the calculator 140 acquires the first displacement End from a first displacement detector 136 and acquires the second displacement Enc2 from a second displacement detector 138. In step S22, the calculator 140 calculates a first temporary drive amount D1 as a temporary drive amount of the knob on the basis of the first displacement by use of the above-mentioned relation between the first displacement Enc1 and the drive amount of the knob. Furthermore, the calculator 140 calculates a second temporary drive amount D2 as the temporary drive amount of the knob on the basis of the second displacement Enc2 by use of the above-mentioned relation between the second displacement Enc2 and the drive amount of the knob.

In step S23, the calculator 140 selects a conversion equation on the basis of the first temporary drive amount D1 and the second temporary drive amount D2 with reference to, for example, Table 2, similarly to Table 1, as described in the following, in the same manner as in the first embodiment.

TABLE 2

| First temporary drive amount | Second temporary drive amount | Value processing method |
|---|---|---|
| $D_1 \geq a$ | $D_2 \geq a$ | Use value of $D_2$ |
| $b < D_1 < a$ | $D_2 \geq a$ | |
| $D_1 > a$ | $b < D_2 < a$ | Use weighted average value |
| $b < D_1 < a$ | $b < D_2 < a$ | |
| $b < D_1 < a$ | $D_2 < b$ | |
| $D_1 \leq b$ | $b < D_2 < a$ | Use value of $D_1$ |
| $D_1 \leq b$ | $D_2 \leq b$ | |

In step S24, the calculator 140 determines a drive amount D of the drive portion 132 on the basis of the first temporary drive amount D1 and the second temporary drive amount D2. For example, when the first temporary drive amount D1 suitably indicates the drive amount D, the first temporary drive amount D1 is determined as the drive amount D, and when the second temporary drive amount D2 suitably indicates the drive amount D, the second temporary drive amount D2 is determined as the drive amount D. Based on a condition between these conditions, a weighted average of the first temporary drive amount D1 and the second temporary drive amount D2 is determined as the drive amount D.

In step S25, the calculator 140 outputs the determined drive amount D. In step S26, the calculator 140 determines whether or not an instruction of the end of the processing is input. When the instruction of the end is not input, the processing returns to the step S21, and when the instruction of the end is input, the processing is ended.

According to the present modification, the drive amount D of the drive portion 132 is output from the calculator 140. The drive amount D is presented to, for example, the user, so that a user's operation can be assisted, or the drive amount D can be used in control of the system. Furthermore, a value closer to a realistic drive amount is used or a weighted average is obtained on the basis of the first temporary drive amount D1 and the second temporary drive amount D2, so that the drive amount can accurately be calculated. It is to be noted that in the present embodiment, the user rotates the knob of the drive portion 132, but the drive portion 132 may be configured to include an actuator or a motor.

As described above, for example, the drive amount functions as the operation assist information. As in the first embodiment and the present modification, the operation assist information can correspond to various pieces of information. For example, the displacements of the first wire 122 and the second wire 124 themselves can be the operation assist information, and a wire value calculated on the basis of the displacements of the first wire 122 and the second wire 124; for example, a shape of the bending portion 115, a pulling force of the wire or stress to be applied to the bending portion 115 functions as the operation assist information.

Second Embodiment

A second embodiment will be described. Here, an aspect different from the first embodiment will be described, the same parts are denoted with the same reference symbols, and the descriptions thereof are omitted. In the first embodiment, the calculator 140 determines the bending amount of the bending portion 115 on the basis of the combination of the value of the first temporary bending amount $\theta_1$ and the value of the second temporary bending amount $\theta_2$. In contrast to the above, in the present embodiment, a calculator 140 selects one of a value of a first temporary bending amount $\theta_1$ and a value of a second temporary bending amount $\theta_2$ as a bending amount of a bending portion 115. In the present embodiment, the calculator 140 uses a condition that a difference between the first temporary bending amount $\theta_1$ and the second temporary bending amount $\theta_2$ is a predetermined value or less, when a state where the bending amount is determined on the basis of the first temporary bending amount $\theta_1$ is changed to a state where the bending amount is determined on the basis of the second temporary bending amount $\theta_2$.

Figure 12A:
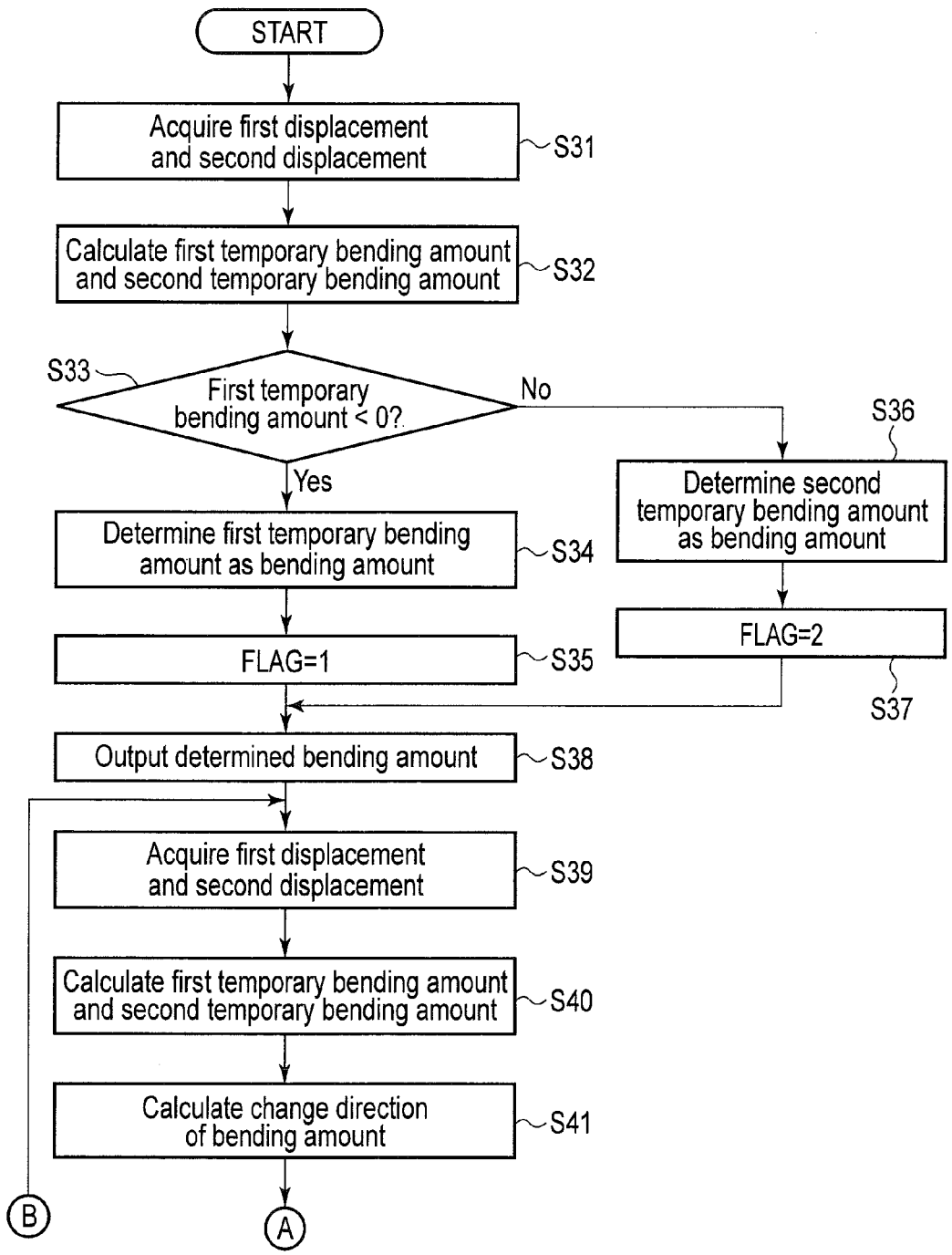
FIG. 12A is a flowchart showing an example of processing by a calculator in a bending operation system according to a second embodiment.

An example of processing of the calculator 140 according to the present embodiment is shown in FIG. 12A and FIG. 12B. In step S31, the calculator 140 acquires a first displacement End from a first displacement detector 136, and acquires a second displacement Enc2 from a second displacement detector 138. In step S32, the calculator 140 calculates the first temporary bending amount $\theta_1$ on the basis of the first displacement Enc1 and calculates the second temporary bending amount $\theta_2$ on the basis of the second displacement Enc2.

In step S33, the calculator 140 determines whether or not the first temporary bending amount $\theta_1$ is smaller than 0. When the first temporary bending amount $\theta_1$ is smaller than 0, the processing goes to step S34. In step S34, the calculator 140 determines the first temporary bending amount $\theta_1$ as a bending amount of the bending portion 115. In step S35, the calculator 140 substitutes 1 into a variable FLAG indicating that the existing bending amount is determined on the basis of the first temporary bending amount $\theta_1$ or the second temporary bending amount $\theta_2$. Afterward, the processing goes to step S38. On the other hand, when it is determined in step S33 that the first temporary bending amount $\theta_1$ is not smaller than 0, the processing goes to step S36. In step S36, the calculator 140 determines the second temporary bending amount $\theta_2$ as the bending amount of the bending portion 115. In step S37, the calculator 140 substitutes 2 into the variable FLAG. Afterward, the processing goes to the step S38. In step S38, the calculator 140 outputs the determined bending amount of the bending portion 115.

In step S39, the calculator 140 acquires the first displacement End from the first displacement detector 136 and acquires the second displacement Enc2 from the second displacement detector 138. In step S40, the calculator 140 calculates the first temporary bending amount $\theta_1$ on the basis of the first displacement Enc1 and calculates the second temporary bending amount $\theta_2$ on the basis of the second displacement Enc2.

In step S41, the calculator 140 compares the previously acquired first temporary bending amount $\theta_1$ and second temporary bending amount $\theta_2$ with the presently acquired first temporary bending amount $\theta_1$ and second temporary bending amount $\theta_2$, to calculate whether the bending amount of the bending portion 115 is increasing or decreasing, i.e., whether the bending portion is bending in a positive bending direction or a negative bending direction.

In step S42, the calculator 140 determines whether or not the first temporary bending amount $\theta_1$ is larger than a second threshold value b and smaller than a first threshold value a and the second temporary bending amount $\theta_2$ is larger than the second threshold value b and smaller than the first threshold value a. When the conditions in the determination of the step S42 are satisfied, the processing goes to step S43.

When the conditions are not satisfied in the determination of the step S42, the processing goes to step S50.

In step S43, the calculator 140 determines whether or not a difference between the first temporary bending amount $\theta_1$ and the second temporary bending amount $\theta_2$ is smaller than a predetermined set value. When the difference is smaller, the processing goes to step S44. When the difference is not smaller, the processing goes to the step S50. In step S44, the calculator 140 determines whether or not the bending amount increases and the variable FLAG=1. When the conditions in the determination of the step S44 are satisfied, the processing goes to step S45. On the other hand, when the conditions are not satisfied in the determination of the step S44, the processing goes to step S47.

In step S45, the calculator 140 determines that the bending amount of the bending portion 115 is the second temporary bending amount $\theta_2$. In step S46, the calculator 140 substitutes 2 into the variable FLAG. Afterward, the processing goes to step S55.

In step S47, the calculator 140 determines whether or not the bending amount decreases and the variable FLAG=2. When the conditions in the determination of the step S47 are satisfied, the processing goes to step S48. On the other hand, when the conditions are not satisfied in the determination of the step S47, the processing goes to step S50. In step S48, the calculator 140 determines that the bending amount of the bending portion 115 is the first temporary bending amount $\theta_1$. In step S49, the calculator 140 substitutes 1 into the variable FLAG. Afterward, the processing goes to the step S55.

In step S50, the calculator 140 determines whether or not the variable FLAG is 1. When the variable FLAG is 1, i.e., when the bending amount of the bending portion 115 is the first temporary bending amount $\theta_1$, the processing goes to step S51. In step S51, the calculator 140 determines that the bending amount of the bending portion 115 is the first temporary bending amount $\theta_1$. In step S52, the calculator 140 substitutes 1 into the variable FLAG. Afterward, the processing goes to the step S55.

When it is determined in step S50 that the variable FLAG is not 1, i.e., when the variable FLAG is 2 and the bending amount of the bending portion 115 is the second temporary bending amount $\theta_2$, the processing goes to step S53. In step S53, the calculator 140 determines that the bending amount of the bending portion 115 is the second temporary bending amount $\theta_2$. In step S54, the calculator 140 substitutes 2 into the variable FLAG. Afterward, the processing goes to the step S55.

In step S55, the calculator 140 outputs the determined bending amount of the bending portion 115. In step S56, the calculator 140 determines whether or not an instruction of the end of the processing is input. When the instruction of the end is not input, the processing returns to the step S39, and when the instruction of the end is input, the processing is ended.

According to the present embodiment, a schematic diagram showing the relation between the first temporary bending amount $\theta_1$, the second temporary bending amount $\theta_2$, and the bending amount of the bending portion 115 which is determined by the calculator 140 compared with the actual bending amount of the bending portion 115 is such a schematic diagram as shown in FIG. 13. FIG. 13 shows an example where the bending amount changes from a negative direction to a positive direction. As shown in the drawing, when the first temporary bending amount $\theta_1$ is larger than the second threshold value b and smaller than the first threshold value a and the second temporary bending amount $\theta_2$ is larger than the second threshold value b and smaller than the first threshold value a (Yes in step S42), the difference between the first temporary bending amount $\theta_1$ and the second temporary bending amount $\theta_2$ is smaller than the predetermined set value (Yes in step S43) and the bending amount increases and the existing bending amount is the first temporary bending amount $\theta_1$ (Yes in step S44), the bending amount is changed from the state where the bending amount is determined on the basis of the first temporary bending amount $\theta_1$ to the state where the bending amount is determined on the basis of the second temporary bending amount $\theta_2$.

Conversely, when the first temporary bending amount $\theta_1$ is larger than the second threshold value b and smaller than the first threshold value a and the second temporary bending amount $\theta_2$ is larger than the second threshold value b and smaller than the first threshold value a (Yes in step S42), the difference between the first temporary bending amount $\theta_1$ and the second temporary bending amount $\theta_2$ is smaller than the predetermined set value (Yes in step S43) and the bending amount decreases and the existing bending amount is the second temporary bending amount $\theta_2$ (Yes in step S47), the bending amount is changed from the state where the bending amount is determined on the basis of the second temporary bending amount $\theta_2$ to the state where the bending amount is determined on the basis of the first temporary bending amount $\theta_1$. In a case other than the above cases, the bending amount is not changed from the state where the bending amount is determined on the basis of the first temporary bending amount $\theta_1$ or the second temporary bending amount $\theta_2$ (the step S50 to the step S54).

According to the present embodiment, the discontinuity of the bending amount determined by the calculator 140 can be set to be small at a negligible degree in accordance with the set value of the step S43. As a result, for example, an operability of the bending portion 115 by the user can be enhanced, and a quality of control of the system can be enhanced.

Third Embodiment

A third embodiment will be described. Here, a different aspect from the first embodiment will be described, the same parts are denoted with the same reference symbols, and the descriptions thereof are omitted. In the first embodiment, the configuration where the bending portion 115 is bent on one flat surface by the first wire 122 and the second wire 124 was described. In contrast to the above, in the present embodiment, a bending operation of a bending portion 115 can be performed in two perpendicular directions. That is, the bending portion can be bent in first and second directions and can further be bent in third and fourth directions perpendicular to the first and second directions. Here, the first and second directions are opposite directions, and similarly the third and fourth directions are opposite directions. The bending portion 115 can be bent not only in the two perpendicular directions but also in all the directions by a combination of the bending operations of the two perpendicular directions. However, the bending portion may be bent only in the two perpendicular bending directions. Furthermore, in the third embodiment, it has been described that the bending operation can be performed in the two perpendicular directions, but the two directions do not have to be perpendicular.

An outline of a configuration example of a bending operation system 200 according to the present embodiment is shown in FIG. 14. As shown in this drawing, the bending operation system 200 has the following in addition to the bending operation system 100 according to the first embodiment. That is, there is provided the bending in the third and fourth directions perpendicular to the bending in the first and second directions in which the bending portion is bent by a first wire 122 and a second wire 124. The bending operation system 200 has a third wire 222 and a fourth wire 224 to bend the bending portion 115 in the third and fourth directions. The third wire 222 and the fourth wire 224 are coupled to each other by a second chain 226 in the same manner as in a configuration where a first wire 122 and a second wire 124 are coupled to each other by a chain 126 (hereinafter, this chain will be referred to as the first chain 126). The second chain 226 engages with a second sprocket provided in a drive portion 132 and the second sprocket is coupled to a second knob. A user rotates the second knob of the drive portion 132 to rotate the second sprocket and displace the second chain 226. In response to the displacement of the second chain 226, the third wire 222 and the fourth wire 224 are displaced and the bending portion 115 is bent in the third or fourth direction. As described above, the third wire 222, the fourth wire 224 and the second chain 226 correspond to the first wire 122, the second wire 124 and the first chain 126, respectively, and function similarly to the wires and chain.

The bending operation system 200 has a third displacement detector 236 to detect a displacement of the third wire 222. The third displacement detector 236 is, for example, an encoder, and an unshown encoder scale is fixed to the third wire 222. The third displacement detector 236 outputs data concerned with the displacement of the third wire 222 to a calculator 140. Similarly, the bending operation system 200 has a fourth displacement detector 238 to detect a displacement of the fourth wire 224. The fourth displacement detector 238 is, for example, an encoder, and an unshown encoder scale is fixed to the fourth wire 224. The fourth displacement detector 238 outputs data concerned with the displacement of the fourth wire 224 to the calculator 140. As described above, the third displacement detector 236 and the fourth displacement detector 238 correspond to the first displacement detector 136 and the second displacement detector 138, respectively, and function similarly to the detectors.

The calculator 140 calculates bending amounts in the third and fourth directions on the basis of outputs of the third displacement detector 236 and the fourth displacement detector 238 in the same manner as in the first embodiment described with reference to FIG. 7 to FIG. 10. According to the present embodiment, functions and effects similar to those of the first embodiment can be obtained concerning the bending of the bending portion 115 and the determination of the bending amount thereof.

According to the present embodiment, the bending portion 115 is freely bent in the first and second directions and the third and fourth directions, and hence the bending portion 115 can be bent in any direction other than a twist direction of the bending portion 115. Furthermore, according to the present embodiment, the bending amounts in the first and second directions and the third and fourth directions can be calculated. It is to be noted that in the present embodiment, the case of the two bending directions has been described as an example, but the present invention is not limited to the two directions, and is similarly applied to three directions or more. Furthermore, the present embodiment may be configured to output a drive amount of a first knob similarly to the modification of the first embodiment. In the present embodiment, the bending amount may be determined in the same manner as in the second embodiment.

As described above, for example, the third wire 222 functions as a third linear member which has one end connected to the tubular portion and is displaced in the longitudinal direction, thereby transmitting power to bend the bending portion in a third direction different from the first direction and the second direction. For example, the fourth wire 224 functions as a fourth linear member which has one end connected to the tubular portion and is displaced in the longitudinal direction, thereby transmitting power to bend the bending portion in a fourth direction opposite to the third direction. For example, the third displacement detector 236 functions as a third displacement detector which acquires a displacement of the third linear member as a third displacement. For example, the fourth displacement detector 238 functions as a fourth displacement detector which acquires a displacement of the fourth linear member as a fourth displacement.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A bending operation system comprising:
    an elongated tubular portion;
    a bending portion configured to be bendable within a predetermined movable range, the bending portion being included in the tubular portion;
    a first linear member, one end of which is connected to the tubular portion, the first linear member being configured to be displaced in a longitudinal direction to transmit power to bend the bending portion in a first direction;
    a second linear member, one end of which is connected to the tubular portion, the second linear member being configured to be displaced in a longitudinal direction to transmit power to bend the bending portion in a second direction which is opposite to the first direction;
    a drive portion configured to displace the first linear member and the second linear member;
    a first displacement detector configured to acquire a displacement of the first linear member as a first displacement, the first displacement detector detecting the first displacement of the first linear member when the second linear member is pulled to bend the bending portion in the second direction;
    a second displacement detector configured to acquire a displacement of the second linear member as a second displacement, the second displacement detector detecting the second displacement of the second linear member when the first linear member is pulled to bend the bending portion in the first direction; and
    a processor comprising hardware, the processor being configured to calculate operation assist information which includes information indicating a shape of the bending portion, the processor being configured to:
        calculate the operation assist information based on only one of the first displacement and the second displacement when the bending portion is bent as much as a first bending threshold value or more in the first direction,
        calculate the operation assist information based on only an other of the first displacement and the second displacement, when the bending portion is bent as much as a second bending threshold value or more in the second direction,
    wherein the first bending threshold value indicates a state where the bending portion is bent as much as a predetermined amount from a reference position in the first direction, and the second bending threshold value indicates a state where the bending portion is bent as much as a predetermined amount from the reference position in the second direction.

2. The bending operation system according to claim 1, wherein the processor is further configured to calculate the operation assist information by use of both of the first displacement and the second displacement in a state where the bending portion is positioned in at least one of the movable ranges.

3. The bending operation system according to claim 1, wherein determination of whether or not the bending portion is bent as much as the first bending threshold value or more in the first direction and determination of whether or not the bending portion is bent as much as the second bending threshold value or more in the second direction are based on a comparison of the first displacement and the second displacement, or a value obtained based on the first displacement and the second displacement with one or more predetermined threshold values.

4. The bending operation system according to claim 1, wherein the processor is further configured to calculate the operation assist information by use of a function which gives a value indicating the continuous operation assist information in accordance with at least one of the first displacement and the second displacement, when the bending portion is positioned in a range from the first bending threshold value to the second bending threshold value.

5. The bending operation system according to claim 1, wherein the processor is further configured to calculate the operation assist information based on a weighted average of the first displacement and the second displacement by use of a weight function concerned with the first displacement and the second displacement in a state where the bending portion is positioned in at least one of the movable ranges.

6. The bending operation system according to claim 1, wherein
    when a value indicating the operation assist information is A, the first displacement is Enc1, the second displacement is Enc2, a weighted function is f, and a function to obtain a value concerned with the operation assist information for the first displacement or the second displacement is g,
    the processor is further configured to calculate the operation assist information:
    based on A=g(Enc2), when the bending portion is bent as much as the first bending threshold value or more in the first direction;
    based on A=g(Enc1), when the bending portion is bent as much as the second bending threshold value or more in the second direction; and
    based on $$A=f(Enc1,Enc2) \times g(Enc1)+(1-f(Enc1,Enc2)) \times g(Enc2),$$

f=0|the first bending threshold value, and
    f=1|the second bending threshold value, when the bending portion is positioned in a range from the first bending threshold value to the second bending threshold value.

7. The bending operation system according to claim 1, wherein the processor is further configured to
   determine whether a bending amount of the bending portion increases in the first direction or in the second direction, and
   determine whether the operation assist information is to be calculated based on the first displacement or the second displacement, in accordance with the determination of whether the bending amount of the bending portion increases in the first direction or in the second direction, when the bending portion is bent in a range from the first bending threshold value to the second bending threshold value and when a difference between the first displacement and the second displacement is a predetermined value or less, and
   calculate the operation assist information based on the only one of the first displacement and the second displacement.

8. The bending operation system according to claim 1, wherein the operation assist information further includes information indicating a drive amount of the drive portion.

9. The bending operation system according to claim 1, wherein
   the first displacement detector is configured to acquire, as the first displacement, a displacement of the first linear member when the bending portion is bent from a reference position in one of the first direction and the second direction, and
   the second displacement detector is configured to acquire, as the second displacement, a displacement of the second linear member when the bending portion is bent from the reference position in the other direction of the first direction and the second direction.

10. The bending operation system according to claim 1, wherein the first displacement detector and the second displacement detector are configured so that the first displacement detector acquires the first displacement and the second displacement detector acquires the second displacement, in a state where the bending portion is positioned in at least one of the movable ranges.

11. The bending operation system according to claim 1, wherein the first displacement detector and the second displacement detector are disposed in a grasp portion disposed proximally to the tubular portion.

12. The bending operation system according to claim 1, wherein
   the bending portion is disposed at a distal end of the tubular portion, and
   the first displacement detector and the second displacement detector are disposed at an other end of the tubular portion.

13. The bending operation system according to claim 1, further comprising:
   a third linear member, one end of which is connected to the tubular portion, the third linear member being configured to be displaced in a longitudinal direction to transmit power to bend the bending portion in a third direction different from the first direction and the second direction;
   a fourth linear member, one end of which is connected to the tubular portion, the fourth linear member being configured to be displaced in a longitudinal direction to transmit power to bend the bending portion in a fourth direction which is opposite to the third direction;
   a third displacement detector configured to acquire a displacement of the third linear member as a third displacement; and
   a fourth displacement detector configured to acquire a displacement of the fourth linear member as a fourth displacement, wherein
   the drive portion further displaces the third linear member and the fourth linear member, and
   the processor is further configured to calculate the operation assist information by use of one or both of the third displacement and the fourth displacement in accordance with a state of the bending portion.

14. The bending operation system according to claim 1, further comprising a coupling member coupling the other end of the first linear member to the other end of the second linear member,
   wherein the coupling member displaces the first linear member and the second linear member together.

* * * * *